United States Patent
Pazienza

(10) Patent No.: US 11,382,928 B2
(45) Date of Patent: Jul. 12, 2022

(54) NUTRITIONAL COMPOSITION WITH RESISTANT STARCH USEFUL IN THE TREATMENT OF NEOPLASTIC DISEASES

(71) Applicant: Fondazione di Religione e di Culto "Casa Sollievo Della Sofferenza"—Opera di San Pio da Pietrelcina, San Giovanni Rotondo (IT)

(72) Inventor: Valerio Pazienza, San Giovanni Rotondo (IT)

(73) Assignee: Fondazione di Religione e di Culto Casa Sollievo Della Soffernza—Opera di San Pio da Pietrelcina, San Giovanni Rotondo (IT)

( * ) Notice: Subject to any disclaimer, the term of this patent is extended or adjusted under 35 U.S.C. 154(b) by 348 days.

(21) Appl. No.: 16/463,568

(22) PCT Filed: Nov. 27, 2017

(86) PCT No.: PCT/EP2017/080468
§ 371 (c)(1),
(2) Date: May 23, 2019

(87) PCT Pub. No.: WO2018/096131
PCT Pub. Date: May 31, 2018

(65) Prior Publication Data
US 2019/0343866 A1    Nov. 14, 2019

(30) Foreign Application Priority Data
Nov. 28, 2016 (EP) .................................. 16200981

(51) Int. Cl.
| | | |
|---|---|---|
| A61K 31/718 | (2006.01) | |
| A23L 29/219 | (2016.01) | |
| A23L 33/00 | (2016.01) | |
| A61P 35/00 | (2006.01) | |
| A61K 31/14 | (2006.01) | |
| A61K 31/194 | (2006.01) | |
| A61K 31/198 | (2006.01) | |
| A61K 31/716 | (2006.01) | |
| A61K 31/717 | (2006.01) | |
| A61K 33/10 | (2006.01) | |
| A61K 33/42 | (2006.01) | |
| A61K 35/35 | (2015.01) | |
| A61K 36/48 | (2006.01) | |
| A61K 38/17 | (2006.01) | |
| A61K 45/06 | (2006.01) | |

(52) U.S. Cl.
CPC .......... *A61K 31/718* (2013.01); *A23L 29/219* (2016.08); *A23L 33/40* (2016.08); *A61K 31/14* (2013.01); *A61K 31/194* (2013.01); *A61K 31/198* (2013.01); *A61K 31/716* (2013.01); *A61K 31/717* (2013.01); *A61K 33/10* (2013.01); *A61K 33/42* (2013.01); *A61K 35/35* (2013.01); *A61K 36/48* (2013.01); *A61K 38/1709* (2013.01); *A61K 45/06* (2013.01); *A61P 35/00* (2018.01); *A23V 2002/00* (2013.01)

(58) Field of Classification Search
CPC ............ A23V 2002/00; A23V 2200/08; A23V 2200/308; A23V 2250/0616; A23V 2250/156; A23V 2250/1578; A23V 2250/16; A23V 2250/194; A23V 2250/304; A23V 2250/5108; A23V 2250/5114; A23V 2250/5118; A23V 2250/54246; A23V 2250/70; A61K 31/718; A61K 2300/00; A61K 31/14; A61K 31/194; A61K 31/198; A61K 31/716; A61K 31/717; A61K 33/10; A61K 33/42; A61K 35/35; A61K 36/48; A61K 38/1709; A61K 45/06; A23L 29/219; A23L 33/40; A61P 35/00
See application file for complete search history.

(56) References Cited

U.S. PATENT DOCUMENTS

2007/0269580 A1 * 11/2007 Werstak .................. A23L 11/05
426/634

FOREIGN PATENT DOCUMENTS

| WO | 97/34592 A1 | 9/1997 |
|---|---|---|
| WO | 2012/113415 A1 | 8/2012 |
| WO | 2016/042518 A1 | 3/2016 |

OTHER PUBLICATIONS

Kondegowda, S., et al., "Effects of Non-Digestible Carbohydrates on the Growth of Estrogen-Dependent Human Breast Cancer (MCF-7) Tumors Implanted In Ovariectomized Athymic Mice", Nutrition and Cancer, 63(1): 55-64 (2011).

Kondegowda, S., et al., "High Amylose Corn Starch Retarded 7,12-Dimethylbenz[a]Anthracene -Induced Mammary Tumor Development in Female Rats", Nubition Research, pp. 1035-1046 (1997). Retrieved from the Internet: URL:http://ac.els-cdn.com/S0271531797000675/1-s2.0-S0271531797000675-main.pdf? tid=b588d440-3ca0-11e7-96fc-00000aab0f6c&acdnat=1495204839a9b9e5084fdacfc61958c209fa0bf89e, (retrieved on May 19, 2017).

(Continued)

*Primary Examiner* — Aaron J Kosar
(74) *Attorney, Agent, or Firm* — Elmore Patent Law Group, P.C.; Joseph C. Zucchero; Carolyn S. Elmore

(57) ABSTRACT

The present invention relates to novel nutritional compositions useful in the treatment of neoplastic diseases. More specifically, the present invention provides for nutritional composition comprising at least resistant starch, proteins and fats, that is able to retard the cancer growth reducing the inflammatory state of the patient and avoiding chronic weight loss.

12 Claims, 12 Drawing Sheets

(56) References Cited

OTHER PUBLICATIONS

D'Aronzo, M., et al., "Fasting cycles potentiate the efficacy of gemcitabine treatment in in vitro and in vivo pancreatic cancer models," Oncotarget, 6(21): 18545-18557 (2015).
Ricci, M., et al., "The Importance of a Proper Control Diet," Retrieved from the internet: URL:http://www.researchdiets.com/system/resources/BAhbB1sH0gZmik8yMDE1LzAyLzE5LzA5XzEyXzU3XzQxN19XU19UaGVfSWIwb3JOYW5jZV9vZ19hX1Byb3Blcl9Db250cm9sX0RpZXRfV2ViLnBkZg/WS The importance of a Proper Control -Diet-Web.pdf. Rretrieved on May 19, 2017.
Panebianco, C., et al., "Engineered Resistant-Starch (ERS) Diet Shapes Colon Microbiota Profile in Parallel with the Retardation of Tumor Growth in in Vitro and In Vivo Pancreatic Cancer Models," Nutrients, 9(331): 1-16 (2017).
Kasaoka, S., et al., "High Amylose Corn Starch Retarded 7, 12-Dimethylbenz[a]Anthracene -Induced Mammary Tumor Development in Female Rats," Nutrition Research, 17(6): 1035-1046 (1997).
Toden, S., et al., "Differential effects of dietary whey, casein and soya on colonic DNA damage and large bowel SCFA in rats fed diets low and high in resistant starch," British Journal of Nutrition, 97: 535-543 (2007).
Siegel, R., et al., "Cancer Statistics, 2012", A Cancer Journal for Clinicians, 62(1): 10-29 (2012).
Matthews, E. H., et al., "Short-term starvation for cancer control in humans," Experimental Gerontology, 48: 1293 (2013).
Hursting, S. D., et al., "Calorie Restriction, Aging, and Cancer Prevention: Mechanisms of Action and Applicability to Humans," Annu. Rev. Med., 54: 131-152 (2003).
Raffaghello, L., et al., "Starvation-dependent differential stress resistance protects normal but not cancer cells against high-dose chemotherapy," PNAS, 105(24): 8215-8220 (2008).
Pazienza, V., et al., "Identification and Functional Characterization of Three NoLS (Nucleolar Localisation Signals) Mutations of the CDC73 Gene," PLoS ONE 8(12): e82292 (2013).
Benegiamo, G., et al., "DNA Methyltransferases 1 and 3b Expression in Huh-7 Cells Expressing HCV Core Protein of Different Genotypes," Dig. Dis. Sci., 2012.
Rappa, F., et al., "Immunopositivity for Histone MacroH2A1 Isoforms Marks Steatosis-Associated Hepatocellular Carcinoma," PLoS One, 8(1): 1-10 (2013).
Adamberg, S., et al., "Degradation of fructans and production of propionic acid by Bacteroides thetaiotaomicron are enhanced by the shortage of amino acids," Frontiers in Nutrition, Nutrigenomics, 1(Article 21) (2014).
Kabanova, N., et al., "Microcalorimetric study of growth of Lactococcus lactis IL1403 at different glucose concentrations in broth," Thermochimica Acta, 496: 87-92 (2009).
Klindworth, A., et al., Evaluation of general 16S ribosomal RNA gene PCR primers for classical and next-generation sequencing-based diversity studies, Nucleic Acids Research, 41(1): 1-11 (2013).
Xia, J., et al., "MetaboAnalyst 3.0—making metabolomics more meaningful," Nucleic Acids Research, vol. 43: W251-W257 (2015).
Apontes, P., et al., "Exploring long-term protection of normal human fibroblasts and epithelial cells from chemotherapy in cell culture," Oncotarget, 2(3): 222-233 (2011).
Liu, Y., et al., "Dietary energy restriction inhibits ERK but not JNK or p38 activity in the epidermis of SENCAR mice," Carcinogenesis, 22(4): 607-612 (2001).
Longo, V., D., et al., "Intermittent supplementation with rapamycin as a dietary restriction mimetic," Aging, 3(11): 1-2 (2011).
Nugent, A. P., "Health properties of resistant starch," Nutrition Bulletin, 30: 27-54 (2005).
Sajilata, M.G., et al., "Resistant Starch—A Review," Comprehensive Reviews in Food Science and Food Safety, 5: 1-17 (2006).

* cited by examiner

Figura 8 M

Figure S1
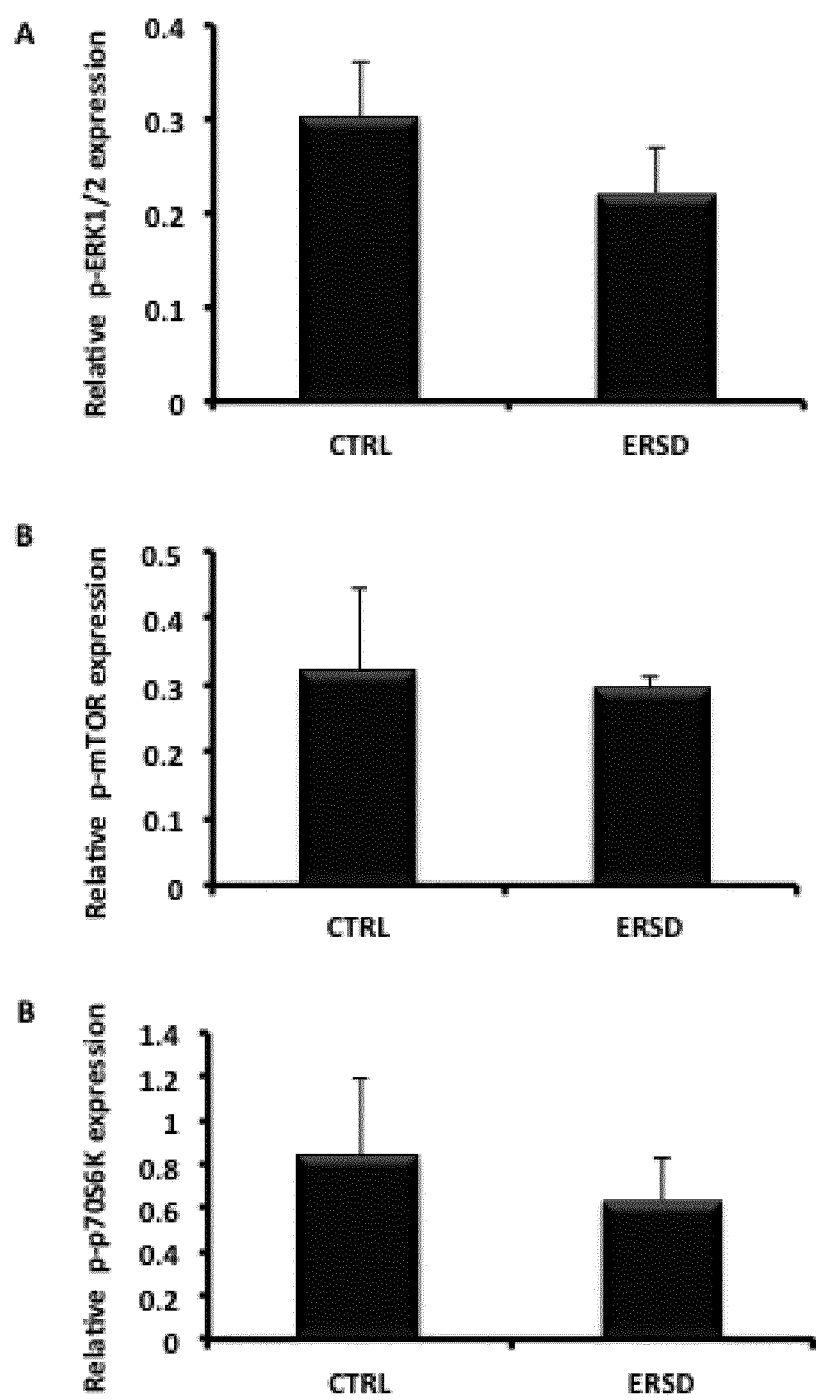

NUTRITIONAL COMPOSITION WITH RESISTANT STARCH USEFUL IN THE TREATMENT OF NEOPLASTIC DISEASES

BACKGROUND OF THE INVENTION

Being the fourth cause of death for cancer worldwide, adenocarcinoma of the pancreas is a highly lethal tumor [1]. Surgical resection is the only curative treatment option, but unfortunately only a small percentage of patients are eligible because diagnosis often occurs late, when the disease is at an advanced stage. Poor survival rates are also due to cancer aggressiveness and chemo-resistance, which make the existing systemic therapies ineffective. Despite both intrinsic and acquired resistance mechanism decrease drug efficacy, gemcitabine, alone or in combination with other drugs, has long been considered the first-line option in the therapy of pancreatic cancer (PC). Our recent breakthrough studies uncovered a potential link between short cycles of fasting and improved effectiveness of chemotherapy [2]. Specifically, short term (24 h) starvation achieved with fasting mimicking medium, increases the uptake of gemcitabine by tumor cells, rendering them more susceptible to drug-induced cell death.

Consistently, in an in vivo model of xenograft pancreatic cancer, gemcitabine administered to 24 h fasted mice significantly decreased tumor volume as compared to control mice. In addition, fasting mimicking medium was shown to shift cells to G0/G1 phase of the cell cycle. Consistently, fasting cycles decrease the levels of the proliferation marker Ki67 in vivo, in agreement with the finding that calorie restriction decreases murine and human pancreatic cell growth. In light of these observations, fasting could reduce cancer growth and increase the effectiveness of chemotherapy also in patients with PC. However, shifting this therapeutic approach from animals to humans has to deal with some objective difficulties: diseased people may refuse to follow the fasting regimen [3] and fasting may worsen the weight loss often occurring in cancer patients. Therefore, alternative approaches are needed to take advantage of the benefits of calorie restriction without requiring special waivers from the patients. In this regard, we focused on nutritional carbohydrates, recognized as pivotal elements in the metabolism of cancer cells and as promoters of cancer growth.

We formulated a nutritional composition, defined an engineered resistant-starch (ERS) diet in which corn starch was replaced by resistant starch. While common starch is metabolized by the enzymes of the small intestine to release glucose, resistant starch is not digestible so it reaches the large intestine where it is fermented by resident bacteria to produce bioactive metabolites such as short chain fatty acids (acetate, propionate, butyrate, valerate), other organic acids (lactate, succinate and formate), gases and alcohols. It is known that diet can shape the composition of the gut microbiota, whose alterations are increasingly emerging as a key factor in the development of gastrointestinal diseases and metabolic disorders as well as of either intestinal and extra-intestinal cancers. Several studies have revealed a link between alterations in oral and gut microbiota composition and the development of pancreatic cancer, which is likely due to the ability of certain bacterial populations to sustain cancer-promoting inflammation. Furthermore, it is nowadays accepted that nutritional restriction has beneficial health effects, including increased lifespan and cancer prevention [4]. Recent studies by our and other groups revealed an association between calorie restriction achieved with fasting and better response to chemotherapy in certain kinds of cancer, among which the pancreatic one, as demonstrated both in vitro and in animal models. This nutritional intervention may potentially reveal useful in fighting human cancers too, but the difficulty for the patient to accept this regimen and the potential worsening of the cancer-related weight loss make the adoption of new approaches necessary.

There is therefore the need of a new nutritional composition that is able to mimic the fasting condition in order to reduce the inflammation state and to retard the tumor growth.

Figure 1:
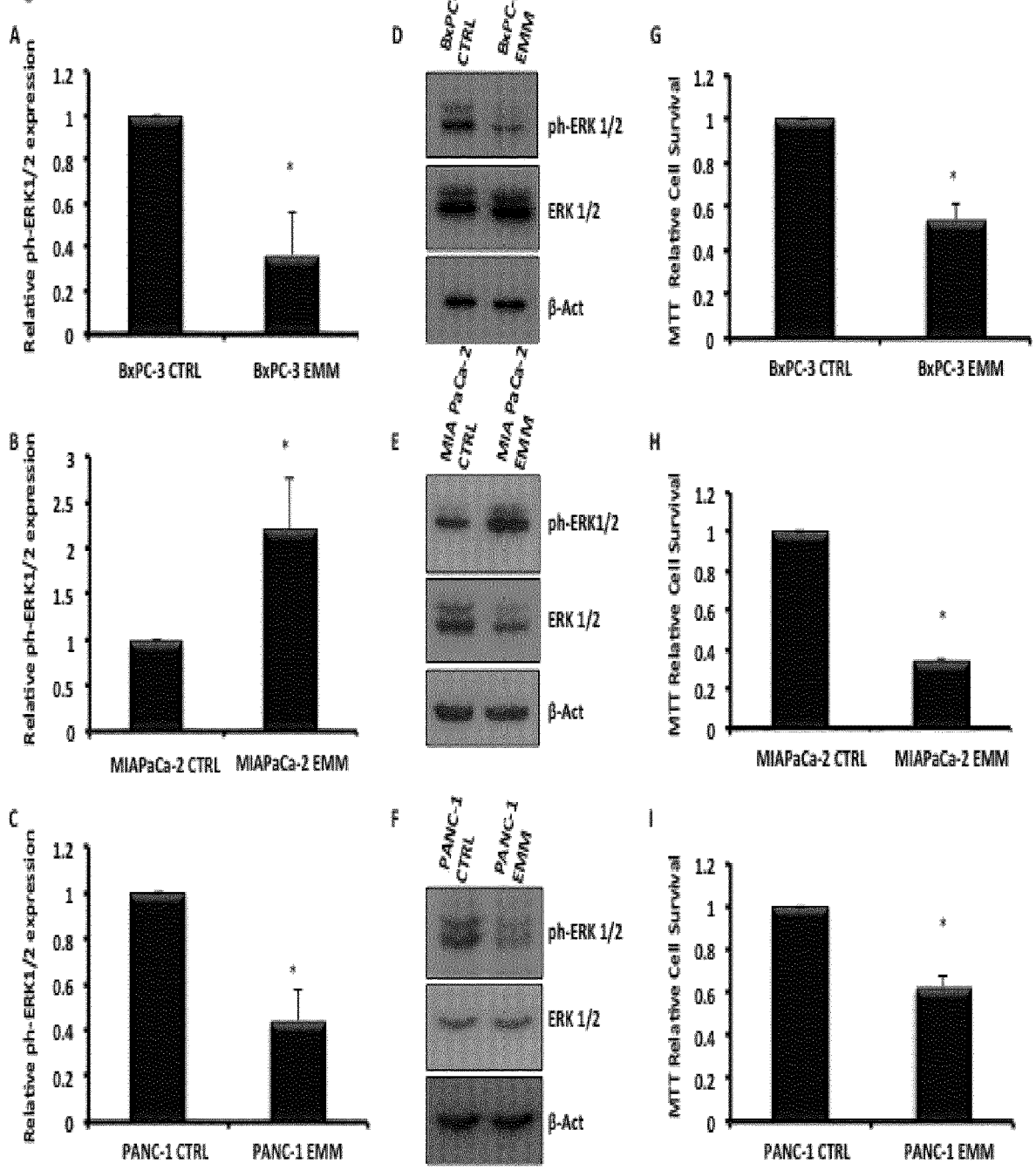
FIG. 1. Quantification of relative phospho-ERK1/2 normalized to total ERK1/2 protein expression (A-B-C) by immunoblot (D-E-F) in control PC cells or treated with ERS mimicking diet for 48 h (Table 1). Cell viability assay in control BxPC-3, MiaPaca-2 and PANC-1 cells or treated for 48 h with ERS mimicking diet (G-H-I). Results are expressed as means±SD. Differences were considered as significant when $P<0.05$ (*) or $P<0.01$ () or $P<0.001$ (*).

Supplementary FIG. 1 (S1). Quantification of immunoblot detection of relative phospho-ERK1/2 normalized to total ERK1/2 (A), phospho-mTOR normalized to total mTOR (B) and phospho-p70S6K normalized to total p70S6K protein expression (C) in control xenograft PC mice' biopsies and mice fed with ERS diet.

Figure 2:
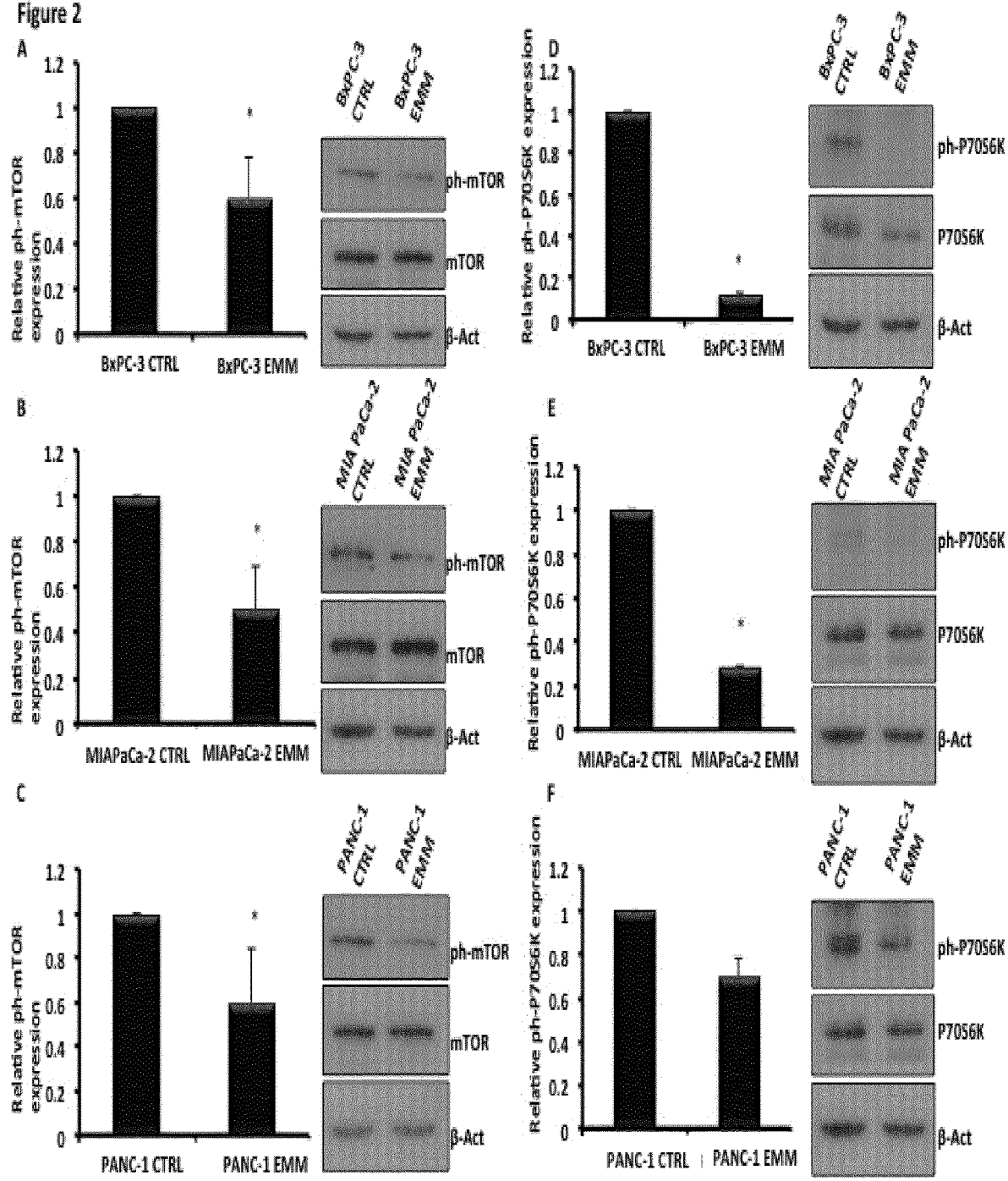

FIG. 2. Quantification and immunoblot detection of relative phospho-mTOR normalized to total mTOR protein expression (A-B-C) in control PC cells or treated with ERS mimicking diet for 48 h. Quantification and immunoblot detection of relative phospho-p70S6K normalized to total p70S6K protein expression (D-E-F) in control PC cells or treated with ERS mimicking diet for 48 h. Results are expressed as means±SD. Differences were considered as significant when $P<0.05$ (*) or $P<0.01$ () or $P<0.001$ (*).

Figure 3:
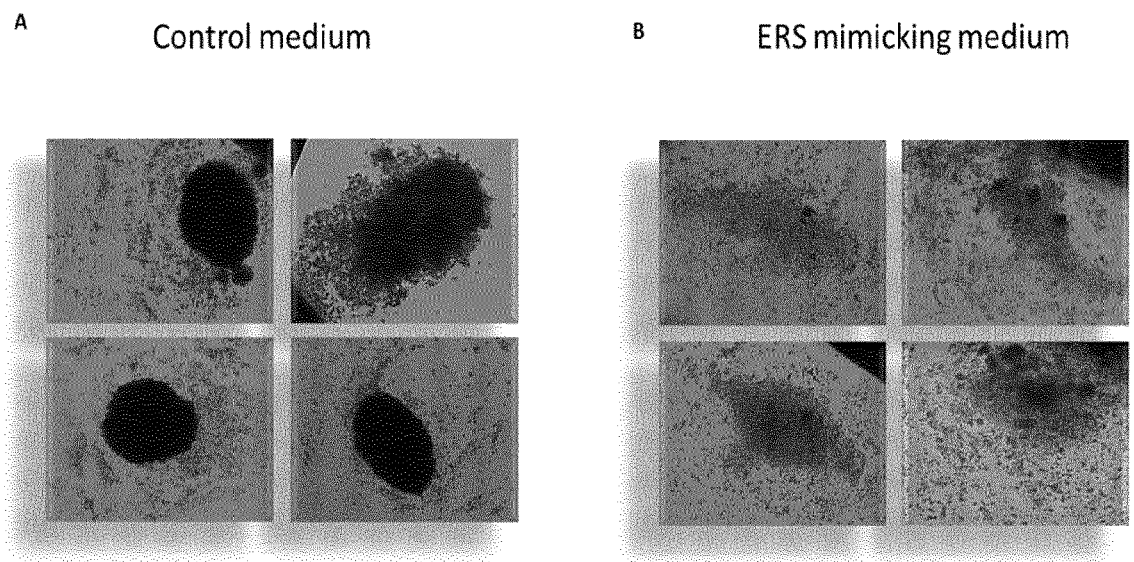

FIG. 3. Effect of control diet (A) and ERS mimicking diet (B) on BxPC-3 cell-cell aggregation and tumor density evaluated by hanging drop assay. Representative images are shown.

Figure 4:
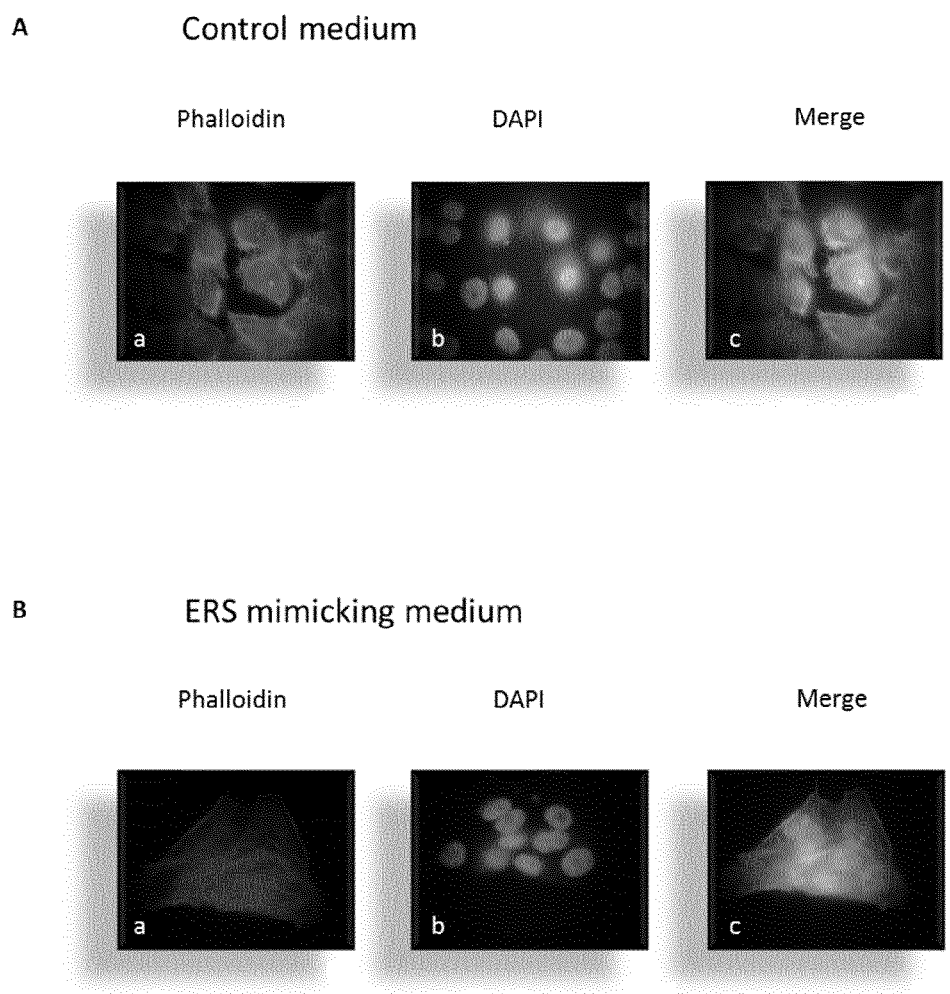

FIG. 4. Fluorescent staining of Phalloidin (a), DAPI (b) and merged signals (c) showing different invadopodia formation in pancreatic BxPC3 cell line, under control diet (A) and ERS mimicking diet (B). Representative images are shown.

Figure 5:
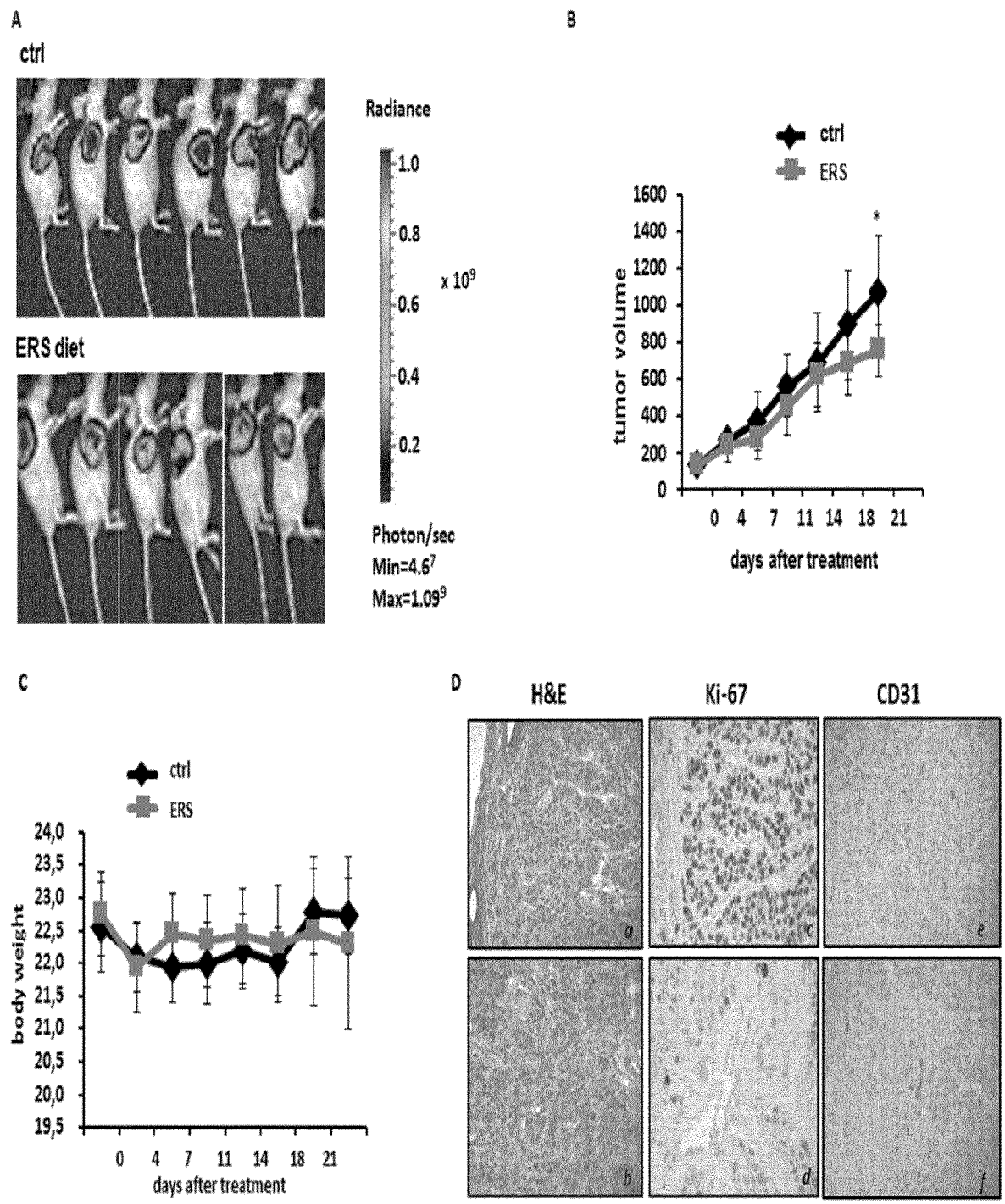

FIG. 5. Effect of ERS diet on PC tumor. BxPC-3-luc tumor-bearing nude mice were randomly assigned into 2 groups when tumor size reached an average volume of 100 mm³. Group 1 (control diet), group 2 (ERS diet). Bioluminescence signaling measured as photons/sec (A). The tumor masses were harvested and tumor volume was evaluated (B). Body weight was also evaluated (C).

H/E, Ki67 and CD31 staining of PC biopsies of mice belonging to the two different groups (D). a, c, e—control diet, b, d, f—ERS diet.

Figure 6:
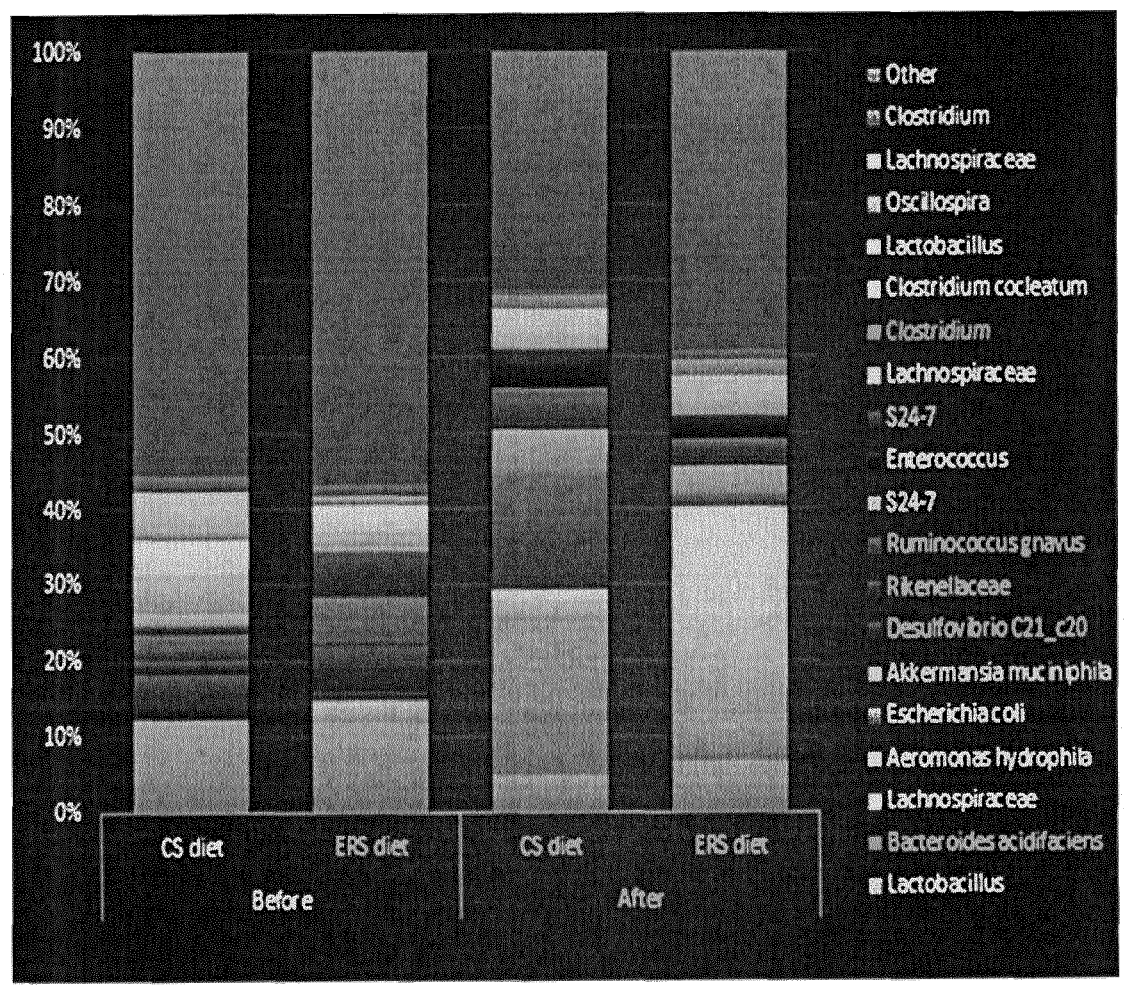
Figure 6:
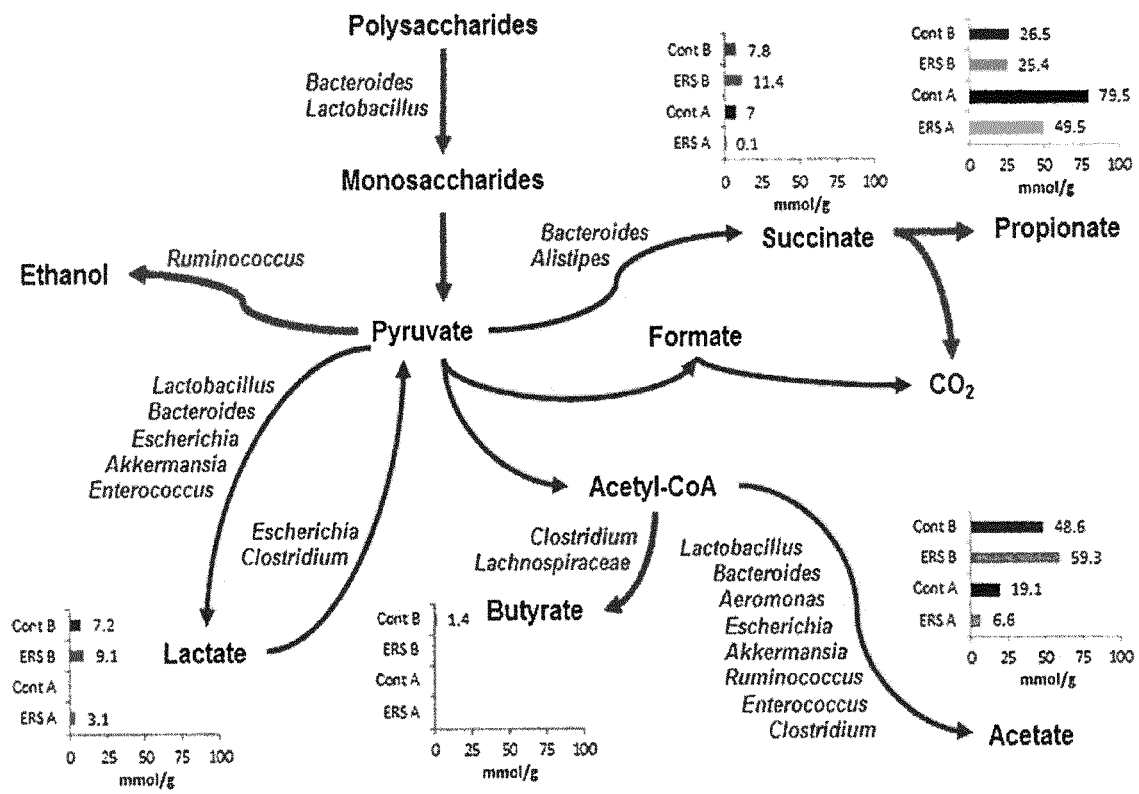

FIG. 6. Composition of bacterial taxa in individual fecal samples. Panel (A) shows the most abundant 20 bacterial taxa of fecal samples with average abundance at least 1% (average sum of reads in relative scale, %). Before and after indicate time when samples are taken in respect to cancer treatment. (B) Metabolic scheme and amount of organic acids in mice fecal samples (mmol/g-feces) before (B) and after (A) the cancer induction. Cont—control diet, ERS— resistant starch diet. Bacterial names on the pathway lines indicate the genera identified from the samples.

Figure 7:
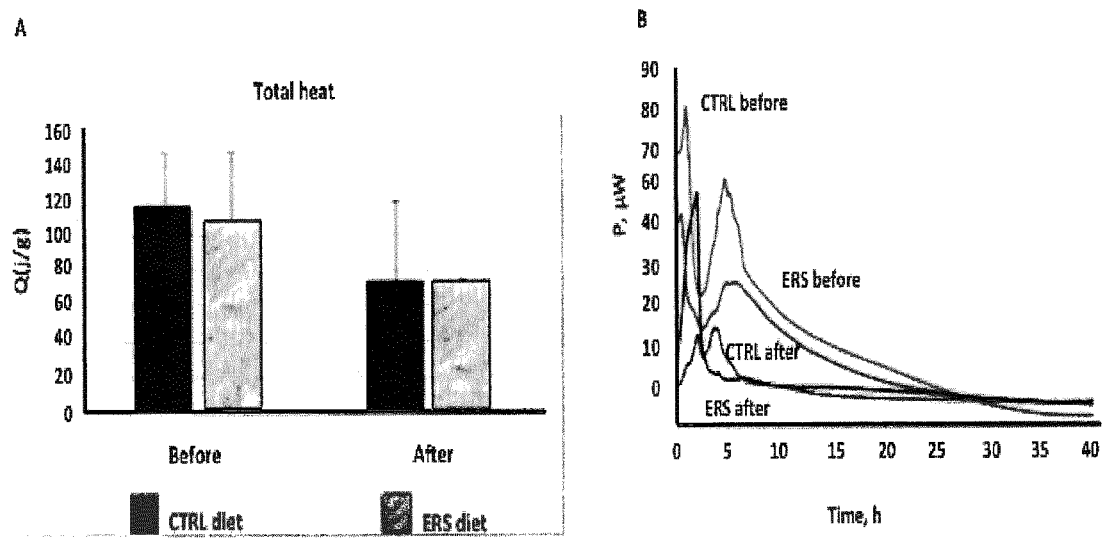

FIG. 7. Total heat accumulated during the growth of fecal consortia in microcalorimetry experiments (A). Total emission of heat of mouse fecal sample was measured and normalized to sample weight. Before—before cancer treatment, After—after cancer treatment. Error bars represent SD. (B) Heat evolution patterns during the growth of fecal consortia in microcalorimeter without added substrate. 'Cont before' or 'Cont after' indicates the fecal sample of mice before or after cancer induction, respectively. ERS—resistant starch diet.

Figure 8:
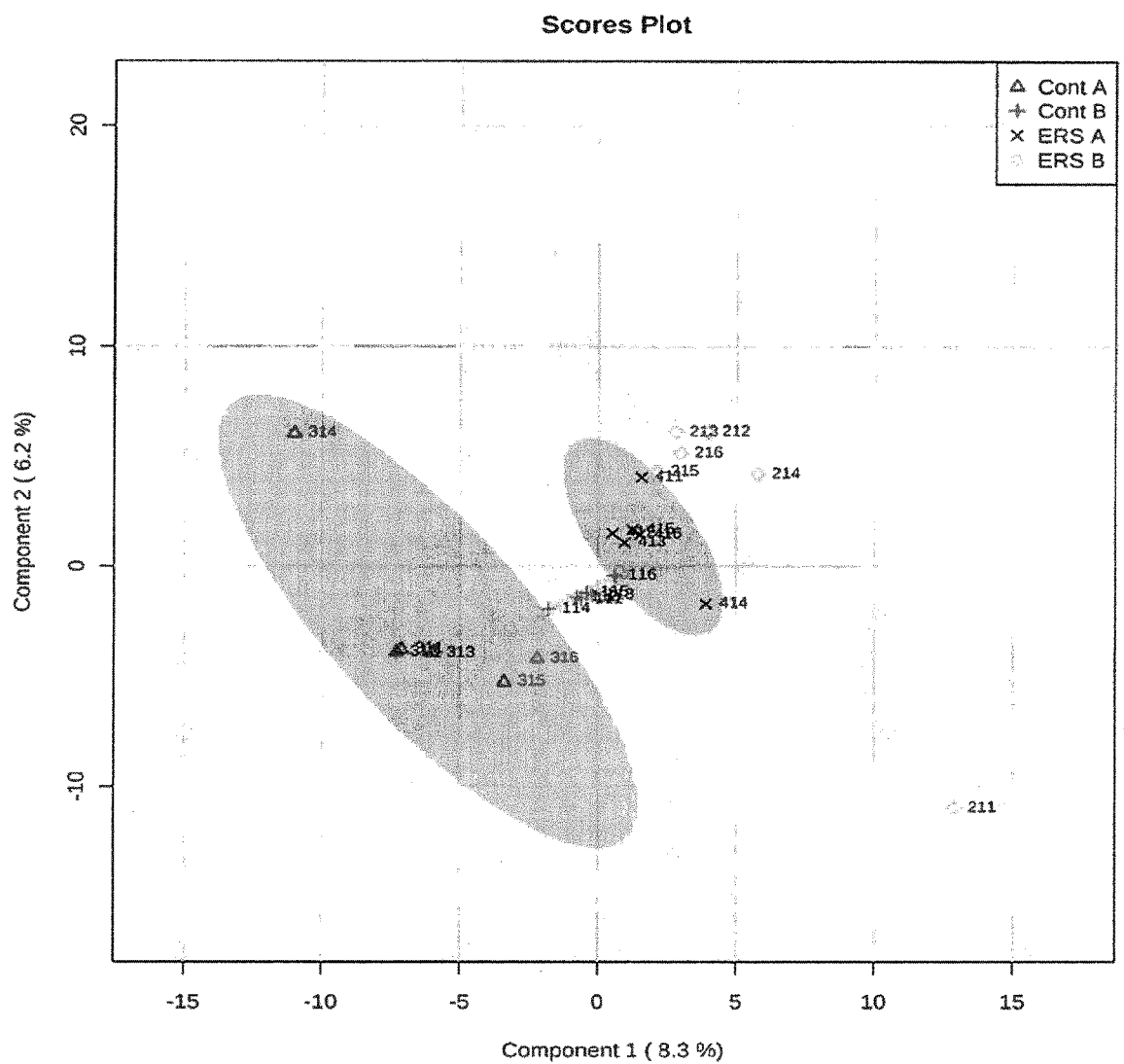
Figure 8:
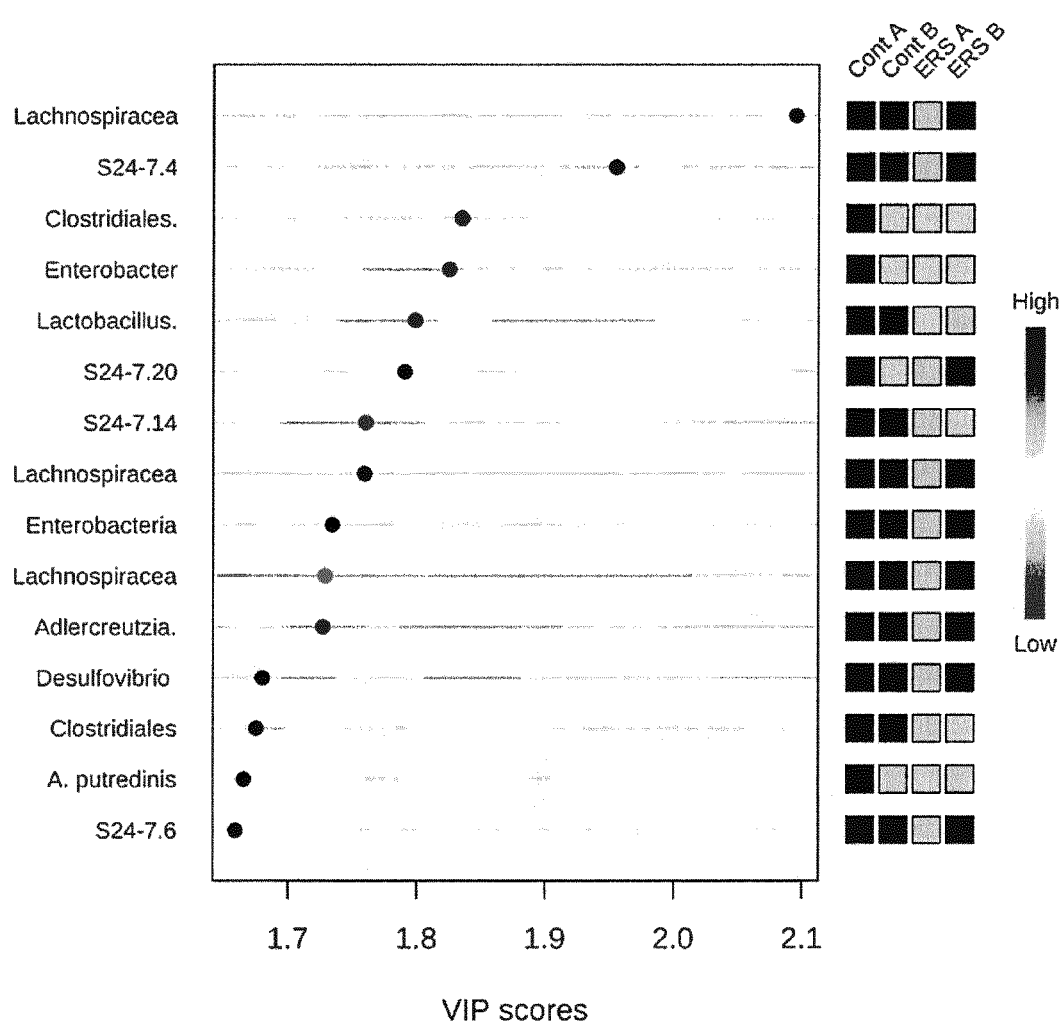
Figure 8:
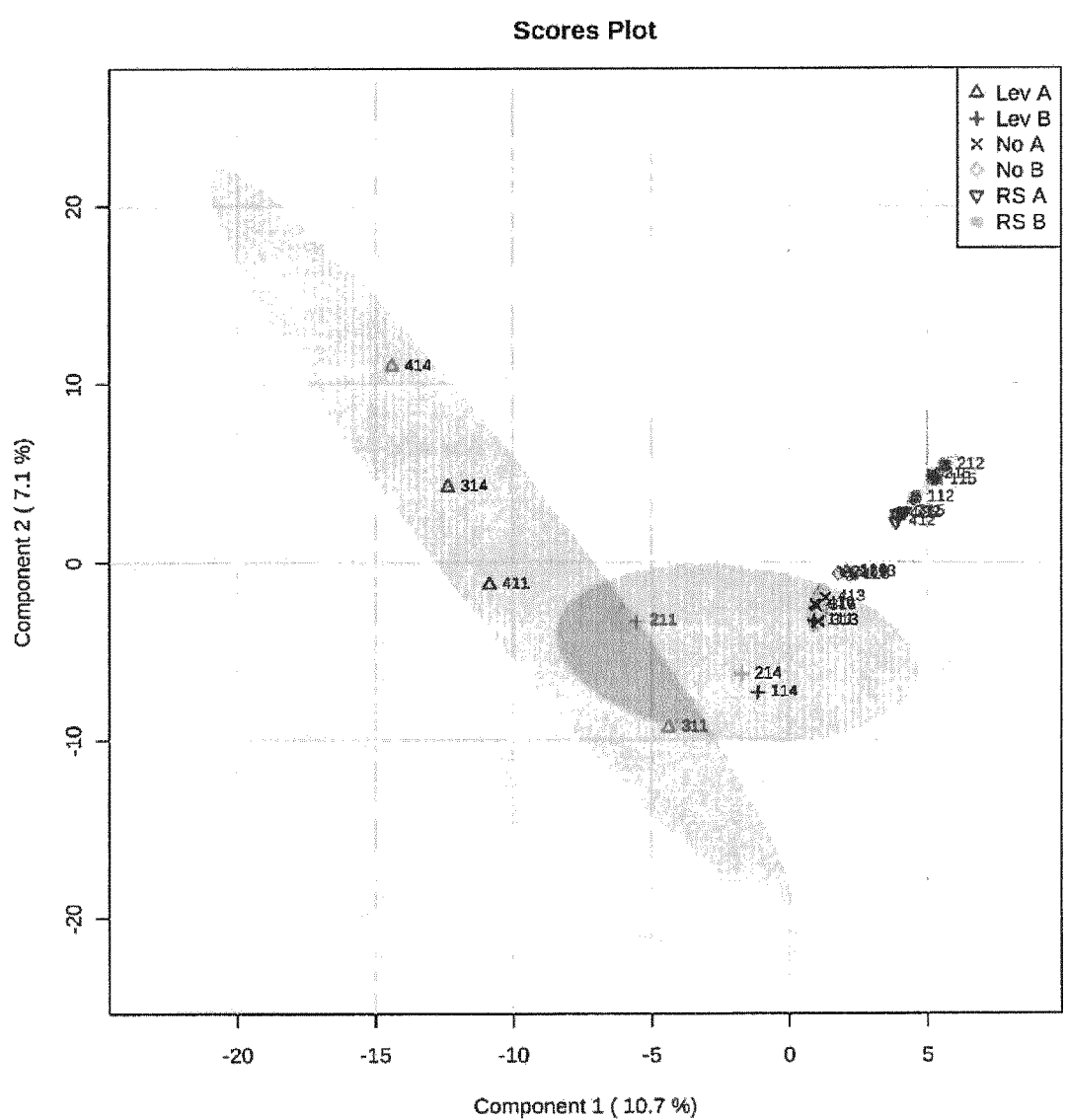

FIG. 8. Score plots of PLS-DA (A and Q) and VIP scores (B and M) grouped by substrates used in microcalorimetry. Plots derived from the integrated analysis of microcalorimetric data (total heat accumulated (Q), maximal heat evolution rate (Pmax), specific growth rate (m)), consumption of substrates (levan, amino acids) and formation of products (organic acids, gases and ethanol), and the bacterial genera grown in the microcalorimetry experiments. Analysis was done by MetaboAnalyst 3.0 program. Lev, NO RS indicate levan no added substrate and resistant starch used in microcalorimetry experiment. A and B in the names shows parallels.

DEFINITIONS

Unless otherwise defined, all terms of art, notations and other scientific terminology used herein are intended to have the meanings commonly understood by those persons skilled in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "resistant starch" herein refers to starch and starch degradation products that escape from digestion in the small intestine of healthy individuals. Resistant Starch has been categorized into four types [16, 17]:
  RS1—Physically inaccessible or undigestible resistant starch, such as that found in seeds or legumes and unprocessed whole grains.
  RS2—Resistant starch is inaccessible to enzymes due to starch conformation, as in high amylose corn starch.
  RS3—Resistant starch that is formed when starch-containing foods are cooked and cooled, such as pasta. Occurs due to retrogradation, which refers to the collective processes of dissolved starch becoming less soluble after being heated and dissolved in water and then cooled.
  RS4—Starches that have been chemically modified to resist digestion.

The term "fat" also known as triglyceride, herein refers to esters of three fatty acid chains and the alcohol glycerol.

The term "physiologically acceptable excipient" herein refers to a substance devoid of any pharmacological effect of its own and which does not produce adverse reactions when administered to a mammal, preferably a human being. Physiologically acceptable excipients are well known in the art and are described, for example, in the Handbook of Pharmaceutical Excipients, sixth edition (2009), which has been incorporated herein for reference purposes.

The term "salts and/or pharmaceutically acceptable derivatives" herein refers to those salts or derivatives which have the biological effectiveness and the properties of the salified or derivate compound and which do not produce adverse reactions when administered to a mammal, preferably a human being. The pharmaceutically acceptable salts may be inorganic or organic salts; examples of pharmaceutically acceptable salts include, but are not limited to: carbonate, hydrochloride, hydrobromide, sulphate, hydrogen sulphate, citrate, maleate, fumarate, trifluoroacetate, 2-naphthalenesulfonate, and paratoluenesulfonate. More information on the pharmaceutically acceptable salts can be found in the Handbook of pharmaceutical salts, P. Stahl, C. Wermuth, Wiley-VCH, 127-133, 2008, incorporated herein for reference purposes. The pharmaceutically acceptable derivatives include esters, ethers, and N-oxides.

The term "simultaneous, separate, or sequential use" herein refers to the simultaneous administration of the first and second compound, or administration in such a way that the two compounds act in the patient's body simultaneously or administration of one compound after the other compound so as to provide a therapeutic effect. In some embodiments, the compounds are taken with a meal. In other embodiments, the compounds are taken after a meal, for example 30 minutes or 60 minutes after the meal. In some embodiments, a compound is administered to a patient for a period of time, followed by administration of the other compound.

The terms "comprising", "having", "including" and "containing" should be understood as 'open' terms (i.e. meaning "including, but not limited to") and should also be deemed a support for terms such as "consist essentially of", "consisting essentially of", "consist of", or "consisting of".

DESCRIPTION OF THE INVENTION

It has been surprisingly found that a nutritional composition comprising at least resistant starch, proteins and fats is useful for reducing the tumor growth and inflammation state.

In particular, the results of the study reported in the examples have demonstrated that nutritional interventions may be beneficial in reducing tumor growth and thus may be used in the clinical practice to synergize the conventional therapies.

In the current study we also demonstrated that an engineered diet (ERS Diet) wherein corn starch has been replaced with resistant starch could be a valid alternative to fasting in counteracting pancreatic cancer.

Overall, in the current study the ERS diet was found to influence the composition and the metabolism of the gut microbiota (inhibiting pro-inflammatory bacteria) and this was paralleled by the retard of tumor growth in the PC xenograft mouse model.

Therefore the results of the study demonstrate that nutritional interventions replacing corn starch with resistant starch could be adopted in support of the conventional therapies in the clinical management of pancreatic cancer.

It is therefore an embodiment of the present invention a composition comprising resistant starch, proteins and fat.

According to the present invention resistant starch includes resistant starch of type RS1, resistant starch of type RS2, resistant starch of type RS3 and resistant starch of type RS4, preferably a resistant starch of type RS2.

According to the present invention the proteins comprised in the composition are selected from casein, L-cystine, soy proteins, whey proteins, or a mixture thereof, preferably casein and L-cystine or a mixture thereof.

According to the present invention the fats comprised in the composition are selected from soybean oil, lard, coconut oil, olive oil and butter or a mixture thereof, preferably soybean oil and lard or a mixture thereof.

In a preferred embodiment the resistant starch is present in the aforesaid composition in a weight ratio comprised between 40% and 60%, more preferably between 45% and 55%, with respect to the total weight of the composition.

In a preferred embodiment proteins are present in the aforesaid composition in a weight ratio comprised between 10% and 30%, more preferably between 15% and 25%, with respect to the total weight of the composition In a preferred embodiment fats are present in the aforesaid composition in a weight ratio comprised between 1% and 10% more preferably between 3% and 5%, with respect to the total weight of the composition.

In a preferred embodiment the composition of the present invention optionally comprises at least one physiologically acceptable excipient.

In a further preferred embodiment, the composition of the present invention comprises additional components, selected from carbohydrates, minerals, salts and/or pharmaceutically acceptable derivatives and vitamins.

Preferably the carbohydrates of the present invention are selected from maltodextrin, cellulose, lactose, sucrose and pectins, preferably maltodextrin and cellulose.

Preferably the salts and/or pharmaceutically acceptable derivatives thereof of the aforesaid composition are selected from dicalcium phosphate, dicalcium carbonate, potassium citrate, sodium chloride, magnesium oxide, magnesium sulphate ammonium molybdate, chromium potassium sulphate, copper carbonate, ferric citrate, manganese carbonate, potassium iodate, sodium fluoride, sodium selenite and/or zinc carbonate, more preferably dicalcium phosphate, dicalcium carbonate and/or potassium citrate.

Preferably the vitamins of the aforesaid composition are selected from Vitamin A, Vitamin D3, Vitamin E, Vitamin B12, Vitamin B6, Vitamin B1, Vitamin B2, menadione, biotin, folic acid, niacin, pantothenic acid, choline bitartrato and/or a mixture thereof.

In a more preferred embodiment the composition of the present invention comprises:
  casein in a weight ratio comprised between 12% and 26%;
  L-cystine in a weight ratio comprised between 0.2 and 0.5%;
  maltodextrin in a weight ratio comprised between 9% and 20%;
  cellulose in a weight ratio comprised between 3% and 6.5%;
  soybean oil in a weight ratio comprised between 1.5% and 3%;
  lard in a weight ratio comprised between 1% and 3%;
  Resistant Starch in a weight ratio comprised between 35% and 70%;
  minerals in a weight ratio comprised between 0.5% and 1.5%;
  dicalcium phosphate in a weight ratio comprised between 0.7 and 2%;
  dicalcium carbonate in a weight ratio comprised between 0.1% and 1%;
  potassium citrate in a weight ratio comprised between 0.9% and 2.2%;
  vitamins in a weight ratio comprised between 0.5% and 1.5%;
  choline bitartrate in a weight ratio comprised between 0.1 and 0.25%; with respect to the total weight of the composition.

A further embodiment of the present invention is the use of said compositions in the treatment of neoplastic diseases, selected from pancreatic cancer, non-small cell lung cancer, breast cancer and ovarian cancer.

Preferably, said neoplastic disease is pancreatic cancer.

According to preferred embodiments, the composition of the present invention is administered orally or parenterally.

Preferably, when the administration of the compositions in the invention is performed orally, the pharmaceutical form may be a tablet, capsule, granules, powder, solution or a suspension, and more preferably, the said oral form may be a tablet, capsule, granules, or a solution.

Preferably, when the administration of the compositions in the invention is performed parenterally, the pharmaceutical form may be an aqueous buffer solution or oily suspension capsule, and more preferably, the said parenteral form may be an oily solution.

In a further object the composition according to the present invention can be administered either combined with or in close temporal proximity to at least one further active principle.

According to a preferred embodiment said active principles are antitumoral agents, preferably nucleoside analogues.

Preferably said nucleoside analogues are selected from gemcitabine, 5-fluoroacile, azacitidine, mercaptopurine, capecitabine, cytarabine, doxifluoridine and thioguanine.

In a preferred embodiment the composition of the present invention is a dry powder formulation.

Preferably said dry powder formulation is reconstituted in water.

According to a preferred embodiment, the composition of the present invention, optionally together with at least one physiologically acceptable excipient, are administered daily along the whole duration of the chemotherapy schedule, oral at least 72 hours before each chemotherapy cycle.

According to a preferred aspect, the daily administration envisages one to four doses per day, even more preferably three daily doses for a maximum of 700 gr/die.

According to a further preferred aspect of the invention, the daily administration is continued for a period of at least 15 days, preferably of at least 30 days, and still more preferably of at least 90 days.

According to a further preferred aspect, such administration is continued for a period of at least 35 days, preferably for at least 65 days.

Preferably, said formulation is administered 3 times a day, over the duration of the chemotherapy schedule for at least 2-15 weeks, preferably 12 weeks. If the patients have difficulties to adhere to this regimen a 72 hours cycle with this food before chemotherapy administration is recommended.

An embodiment of the present invention is the use of said formulation in the treatment of neoplastic diseases, selected from pancreatic cancer, non-small cell lung cancer, breast cancer and ovarian cancer.

Preferably said neoplastic disease is pancreatic cancer.

A further embodiment is a food product comprising the composition of the present invention. Preferably said food product is a liquid, a lyophilized, a gel or a solid food product.

A further embodiment of the present invention is the use of said food product in the treatment of neoplastic diseases, selected from pancreatic cancer, non-small cell lung cancer, breast cancer and ovarian cancer, preferably pancreatic cancer.

A further embodiment is a kit comprising a first container (a) containing the composition of the present invention and a second container (b) containing water.

Materials and Methods

1. Cell Culture and ERS Mimicking Condition

BxPC-3 and PANC-1 cells were cultured either in control DMEM medium (CM) 2 g/L glucose supplemented with 10% fetal bovine serum (FBS), 100 U/ml penicillin and 100 µg/ml streptomycin (Invitrogen Life Technologies, Milan, Italy) in 5% CO2 atmosphere at 37° C. or in ERS mimicking medium (EMM) DMEM (0.5 g/L glucose and 1% FBS) (Table 1). MIAPaCa-2 were maintained in control RPMI 1640 medium (Invitrogen Life Technologies, Milan, Italy) or in ERS mimicking condition RPMI 1640 medium as described elsewhere [5]. Cell proliferation was measured by MTT assay as previously described [6].

TABLE 1

ERS mimicking medium

|  | Ctrl medium | ERSmimicking medium |
|---|---|---|
| DMEM or RPMI 1640 medium | 90% | 98.5% |
| Glucose | 2 g/L | 0.4 g/L |
| Fetal Bovine Serum (FBS) | 10% | 1.5% |
| Penicillin | 100 U/ml | 100 U/ml |
| Streptomycin | 100 µg/ml | 100 µg/ml |

2. Animal Study

The in vivo study was performed in an AAALAC (Association for Assessment and Accreditation of Laboratory Animal Care International) accredited experimental facility. Animal protocols were approved by the Institutional Animal Care and Use Committee. $5 \times 10^6$ BxPC-3-luc cancer cells per mouse were suspended in 0.1 mL of PBS/matrigel mixture (1:1) and then s.c. injected (right flank) into 5-6 weeks old female Nu/Nu nude mice. When tumor size reached an average volume of 100 mm$^3$, BxPC-3-luc tumor-bearing nude mice were randomly assigned into 2 groups (6 mice/group): group 1 (under control diet) and group 2 (under ERS diet). Animals had free access to water. ERS diet pellet consist in replacing the entirely corn starch with resistant starch.

Fresh fecal samples were collected before and after cancer induction from both feeding groups. The fecal samples were collected into a regular sterile 1.5 ml eppendorf and kept frozen at −80° C. until use in cultivation experiments.

TABLE 2

Components present in the ERS diet and in a Control Diet

| Specific ingredients | Control Diet (gr) | ERS Diet (Gr) |
|---|---|---|
| Casein | 200 | 200 |
| L-Cystine | 3 | 3 |
| Corn starch | 550 | 0 |
| Maltodextrin | 150 | 150 |
| Resistant starch | 0 | 550 |
| Cellulose BW200 | 50 | 50 |
| Soybean Oil | 25 | 25 |
| Lard | 20 | 20 |
| Mineral Mix | 10 | 10 |
| DiCalcium Phosphate | 13 | 13 |
| DiCalcium Carbonate | 5.5 | 5.5 |
| Potassium citrate | 16.5 | 16.5 |
| Vitamin Mix | 10 | 10 |
| Choline bitartrate | 2 | 2 |

For the purpose of the present invention a variation of 30-40% of these concentration is considered also to be effective.

3. Immunoblotting

Total protein extraction from pancreatic cancer adherent cells and from snap frozen pancreatic cancer xenograft specimens was obtained using homemade Sample Buffer Laemmli 2× (50 mM Tris-HCl, pH 6.8, 100 mM dithiothreitol, 2% sodium dodecyl sulfate, 0.1% bromophenol blue, 10% glycerol) supplemented with 2× protease inhibitor cocktail (COMPLETE; Roche Diagnostics, Mannheim, Germany), 1 mM phenylmethylsulphonyl fluoride and 1 mM sodium orthovanadate as already described [7]. Equal amount of protein extract for each sample was loaded onto 10% SDS-polyacrylamide gel and transferred on PVDF membrane (Whatman, Dassel, Germany) for 60 min at 60V. Membranes were incubated overnight at 4° C. with primary antibody diluted 1:1000 into Blocking Buffer as reported in [7]. Primary polyclonal rabbit antibody against phospho ERK1/2 (4695), mouse monoclonal antibody against β-Actin (C4) (sc-47778) were from Santa Cruz Biotechnology (D.B.A. Milan, Italy); antibodies against ERK1/2 (4370), mTOR (#2972), phospho-mTOR (#2974), p70S6K (#9202), phospho-p70S6K (#9205) were obtained from Cell Signaling. Before incubation for one hour at room temperature with appropriate secondary antibodies (BioRad, Hercules, Calif. goat anti-mouse and goat-anti-rabbit diluted 1:3000) the membranes were washed three times with washing solution (1× Tris-Buffered Saline, 0.1% Tween 20 Sigma). Detection on X-ray film (Amersham Biosciences) of the antigen-antibody complexes was performed using enhanced chemiluminescence (ECL; Amersham Biosciences) according to the manufacturer's instructions.

4. Hanging Drop Assay

Cultured BxPC-3 cells were harvested, counted and resuspended at a final concentration of $2.5 \times 10^6$ either in control or ERS mimicking medium. Drops (20 µl each) were pipetted onto the inner surface of a Petri dish lid placed so that the drop was hanging from the lid with the cells suspended within it. To avoid evaporation, 8 ml of PBS were placed in the bottom of the Petri dish. After incubation at 37° C. in 5% $CO_2$ atmosphere for 5 days, the cells were photographed using a Nikon Eclipse E600 microscope.

5. Immunofluorescence

BxPC-3 cells, grown on coverslips, were fixed for 10 min in 4% paraformaldehyde at room temperature (RT). Cells were then washed three times in PBS, permeabilized with 0.1% Triton X-100 in PBS for 5 minutes, washed twice again in PBS and incubated with the Alexa-Fluor 555/Phalloidin diluted 1:50 in PBS, 1% bovine serum albumin (BSA), for 30 minutes at RT. After rinsing three times in PBS, coverslips were mounted on microscope slides with DAPI-containing mounting medium. For fluorescence microscopy, slides mounted for immunofluorescence were observed using a Nikon Eclipse E600 microscope.

6. Immunohistochemistry Paraffin-embedded pancreatic mice cancer sections allocated in the two different groups were immunostained by using commercially available detection kit (EnVision™ FLEX+, Dako, Glostrup, Denmark) following the manufacturer's protocol already described [8]. Primary antibodies for Ki67 (cat. no. M7240) and CD31 (cat. no. IR61061) were from Dako. Replacing the primary antibody with normal serum alone was used to check the specificity of all reactions. Positive and negative controls were run concomitantly. Ki67 immunoreactivity was evaluated blindly by an expert pathologist assessing a semiquantitative scoring system in ten high power fields (10HPF, ×400) according to a semiquantitative scale from negative to 3+ (−: 0%; +: 1-33%; ++: 34-66%; +++: 67-100%).

7. Isothermal Microcalorimetry

For inocula preparation, 0.02-0.4 g fecal samples were thawed and mixed with 5 sterile deaerated PBS containing (final concentration, mM): NaCl—160, KCl—3, $Na_2HPO_4$—8, $NaH_2PO_4$—1, pH 7.2, supplemented with freshly made and filter sterilized Cys-HCl (0.5 g/L in final medium) and solution of autoclaved sodium thioglycolate (0.5 g/L in final medium) as reducing agents and 4 ml substrate solution or water (as control without additional carbohydrates). Substrate solution contained 5 g/L of levan prepared as shown in [9] or resistant starch (Tapioca maltodextrin, C1, Cargill; GermanyGmbh). All growth media were pre-reduced in an anaerobic jar (Anaero-Gen™, Gas-Pack System, OxoidInc., UK) before inoculation the fecal cultures.

The 3.3 ml calorimeter ampoules were filled with 2 ml of the inoculated medium, closed hermetically and incubated at 37° C. in a 24-channel isothermal microcalorimeter TAM III (TA Instruments, Delaware, USA) as described in Kabanova et al. [10]. The heat flow (P, µW) was recorded and total heat accumulated (Q, J) that is proportional to biomass amount was calculated by integration of heat flow. All fecal samples were tested at least in duplicate.

8. Determination of Metabolites

Samples from the beginning and end of the growth experiments were analyzed for microbial 16S rDNA sequences and metabolites. The samples were centrifuged (21000 g, 10 min), solution of 10% sulfosalicylic acid was added to the supernatant (1:0.25 vol/vol) and both pellet and supernatant stored at −20° C. until the analysis. Before chromatographic analyses the supernatant samples were centrifuged (21000 g, 15 min, 4° C.) and filtered through 0.20 µm PTFE syringe filters (Millex filters SLLGH13NK, Millipore). The initial (0 h) samples were additionally ultra-filtered using AmiconR Ultra-10K Centrifugal Filter Devices, cut-off 10 kDa (Millipore).

The concentrations of organic acids (succinate, lactate, formate, acetate, propionate, isobutyrate, butyrate, isovalerate, valerate), glycerol and ethanol were determined by high-performance liquid chromatography (HPLC, Alliance 2795 system, Waters, Milford, Mass.), using a BioRad HPX-87H column (Hercules, Calif.) with isocratic elution of 0.005 M $H_2SO_4$ at a flow rate of 0.5-0.6 mL/min at 35° C. Refractive index (RI) (model 2414; Waters) and UV (210 nm; model 2487; Waters) detectors were used for quantification of the substances. Detection limit for the HPLC was 0.1 mM.

9. Microbiome Analyses

DNA was extracted from cell's pellet using MoBioPowerFecal DNA extraction kits (MoBio, Carlsbad, Canada) according to the manufacturer's instructions. Universal primers S-D-Bact-0341-b-S-17 Forward and S-D-Bact-0785-a-A-21 Reverse [published in Klindworth A, Pruesse E, Schweer T, Peplies J, Quast C, Horn M and Glockner F O. Evaluation of general 16S ribosomal RNA gene PCR primers for classical and next-generation sequencing-based diversity studies. Nucleic Acids Res. 2013; 41(1):e1], were used for PCR amplification of the V3-V4 hypervariable regions of 16S rRNA genes. The amplified region was about 450 bp and in average 12000 reads per sample were obtained. The mixture of amplicons was pyrosequenced using IluminaMiSeq 2×250 v2 platform.

Sequence data was analysed using BION-meta, an open source program, according to author's instructions. First, sequences were cleaned at both ends using a cut-off for minimum quality of 95%, followed by removal of shorter reads than 350 bp. Second, sequences were clustered based on a minimum seed similarity of 99.5% (consensus reads). Last, consensus reads were taxonomically aligned to the SILVA reference 16S rDNA database (v123) using match minimum of 90%.

10. Statistical Analysis

Shannon diversity index (H') was calculated according to formula: $H'=-\Sigma_i^R p_i \cdot \ln(p_i)$ where R represented the richness (total number of species identified in the sample) and $p_i$ represented the relative abundance of $i^{th}$ species in the sample. For multivariate analysis, data from all experiments (abundances of bacterial taxa, growth characteristics from calorimetry and metabolite productions/consumptions) was merged into a matrix table. Partial least squares discriminant analysis (PLS-DA) of the data was performed using web-based software MetaboAnalyst 3.0 [12]. For in vitro and mice experiments results are expressed as mean±SD. Comparisons were made using Student's t-test, Differences were considered as significant when $P<0.05$ (*) or $P<0.01$ () or $P<0.001$ (*).

Results

ERK1/2, and mTOR Pathway Detection in Pancreatic Cancer Cells Under ERS Mimicking Culture Conditions As a first step, we hypothesized that the ERS mimicking culture could be responsible for inhibiting the cells' proliferation. To this aim, we assessed the activation of ERK1/2 and mTOR pathways which are well known to be nutrient sensitive and to be involved in proliferation pathways [13-15]. As shown in FIG. 1, ERS mimicking medium significantly inhibits ERK1/2 phosphorylation in Bx-PC3 and PANC-1 cell lines (A-C; D-F) while an increased ERK1/2 phosphorylation level was observed in MiaPaca-2 cells (B). The latter, however, shows a decreased level of ERK1/2 total form (E) by immunoblot analysis. Furthermore all three cell lines showed reduced cell viability as evaluated by MTT assay (FIG. 1 G-H-I). Additionally, when the mTOR pathway was investigated, a reduced level of mTOR phosphorylation was observed in all three cell lines (FIG. 2 A-B-C) with a consequent reduction of its substrate p70S6K phosphorylation (FIG. 2 D-E-F).

Effect of ERS Mimicking Culture Conditions on Cell-Cell Aggregation.

In vivo, solid tumors grow in a three dimensional (3D) spatial conformation resulting in a dissimilar exposure of cells to blood vessels, nutrients and chemotherapeutic compounds. To better mimic the in vivo architecture of organs, we then developed a 3D cell's culture to assess the effect of ERS mimicking diet on cell-cell aggregation. As shown in FIG. 3, in 3D models the ERS mimicking medium (B) inhibits BxPC-3 cells' aggregation as compared to control medium (A). This suggests that, since the cells are more dispersed, chemotherapy could reach them better thus resulting more effective.

Effect of ERS Mimicking Culture Conditions on Invadopodia Formation.

Cell migration and invasion play a key role in the spread of cancer cells during metastasis. Invasive cancer cells reorganize their cytoskeleton and produce membrane protrusions, called invadopodia. In order to assess whether culture conditions could affect cancer cells' invasiveness, in BxPC-3 cells cultured in either control medium or ERS mimicking medium, cytoskeletal actin was stained with fluorescent Phalloidin and pictures were taken at fluorescence microscope. As shown in FIG. 4, cells grown in control medium (A) showed membrane protrusions while cells grown in ERS mimicking conditions (B) did not. This suggests that ERS mimicking medium would decrease the invasive potential of pancreatic cancer cells.

Effect of ERS Diet on Pancreatic Cancer Xenograft Mice Tumor Growth

We then evaluated the effects of ERS diet treatment in a xenograft pancreatic cancer mouse model. As shown in FIGS. 5 (A and B), mice subjected to ERS diet displayed a slight but significant retarded progression of pancreatic cancer tumor (p=0.04) as compared to control mice. No significant differences in total body weight were observed between the two mice groups (FIG. 5C).

We then assessed the expression of proliferation and cell death/apoptosis markers in pancreatic cancer biopsies from mice. Ki67 positivity was higher in mice fed with control diet with 60% of mice displaying the highest positive levels (FIG. 5D panel c) while in ERS diet group 40% of mice were positive for Ki67 staining with the remaining 60% of mice were mildly positive (panel d). Moreover, when staining for neoangiogenesis, using an anti-CD31 antibody, every mouse in control group displayed higher total of CD31 levels (FIG. 5D panel e) as compared to ERSD treated mice (panel f). Additionally, ERK1/2 and mTOR (with its direct substrate p70S6K) were determined by western blot in a subset of mice treated with control diet or ERS diet. As it is shown in supplementary FIG. 1 both pathways tended to be downregulated without reaching a statistical significance.

Characterization of Microbiota and Metabolites of Fecal Samples

In total, 65 bacterial taxa that exceed 0.5% relative abundance in feces of control and/or in ERS diet fed mice were found. Initial composition of fecal consortia was dominated by phylum Firmicutes (over 50%). The major taxa represented in the samples belonged to *Lactobacillus, Lachnospiraceae, Bacteroides, Blautia, Aeromonas* and *Escherichia* (FIG. 6A). The majority of the detected bacteria were present in all fecal samples. However, diversity of microbiota was higher in ERS diet fed mice than that in control group (Shannon indexes 3.56±0.06 and 3.34±0.2, respectively). After the cancer induction diversity of microbiota were decreased, especially in case of control diet compared to ERS diet (Shannon indexes 3.0±0.01 and 3.05±0.18, respectively). *Bacteroides acidifaciens* and *Escherichia* sp. were the dominant species (5-20 and 6-8%, respectively) in cancer xenografted mice fed with control diet while species of *Blautia* and *Aeromonas* were dominant (over 15%) in cancer xenografted mice fed with ERS diet. The only species found only in fecal samples of mice fed with ERS diet and before, but not after cancer induction was *Bacteroides thetaiotaomicron* (relative abundance of 1%). The latter was also detectable in minor amounts (0.1%) in xenografted mice fed with control diet. The metabolite profiles differed between fecal samples depending on the nourish (control vs ERS diet). The main fermentation product before cancer induction was acetate (53 and 56% from all acids produced on control or ERS diet, respectively) followed by propionate, succinate and lactate while butyrate was detected only in negligible amounts (FIG. 6B). After cancer induction significant reduction in acetate production was observed on both diets (2.5 and 9 folds on control and ERS diet, respectively), which was replaced by propionate production especially on control diet. It is remarkable that no lactate was produced by control diet while succinate production was negligible by ERS diet. Total acid production before cancer induction was similar on both diets, however, after the induction it was almost two times reduced on ERS diet from 105 to 59 mmol/gDW but not on control diet.

Table 3 shows the production of organic acids during the growth of fecal microbiota in microcalorimeter without added substrate (mmol/gDW).

TABLE 3

| Sample | Acetate | Butyrate | Formate | Lactate | Propionate | Succinate |
| --- | --- | --- | --- | --- | --- | --- |
| Control diet before | 906 ± 160 | 100 ± 23 | 335 ± 248 | 199 ± 179 | 185 ± 50 | 143 ± 52 |
| Control diet after | 559 ± 3 | — | 260 ± 39 | 51 ± 30 | 133 ± 27 | 74 ± 3 |
| ERS diet before | 922 ± 110 | 33 ± 46 | 353 ± 246 | 160 ± 26 | 88 ± 124 | 131 ± 22 |
| ERS diet after | 533 ± 211 | — | 338 ± 27 | 220 ± 56 | 73 ± 5 | 65 ± 58 |

Growth Experiments with Fecal Microbiota

To elucidate the potential of ERS diet and a polyfructanlevan to modulate the composition and fermentation pattern of the fecal microbiota, in vitro growth experiments were carried out. The growth experiments using fecal inocula from mice after and before cancer induction, were performed in defined medium containing either levan, resistant starch or no additional substrate (control). The heat generation (biomass growth) of the control cultures occurred in the expense of the residual substrates (complex carbohydrates and proteins) in the fecal material, accessible to microorganisms. Two phases can be discriminated on the growth curves with samples taken before the cancer induction (FIG. 7B) but growth of bacteria from samples of cancer induced mice fed by ERS medium was rapid within the single phase indicating fast metabolic rates of bacteria in these samples. There was about 30% difference in accumulated heat between samples collected before and after cancer induction (110-120 vs 74-75 J/g, respectively, FIG. 7A) independently of mice' diets. The change of accumulated heat, between samples of before and after cancer induction, could indicate the modification of the diversity of microbial community (see above). By PLS-DA analysis combining all data (metabolites, heat data and sequencing data) maximal heat evolution rate indicating rapid metabolic activity was the most important parameter discriminating the growth of consortia in microcalorimetry experiments (FIG. 8). Additionally two other important parameters having high VIP scores were relative abundance of *C. cocleatum*, which was high on RS and formate production, which was high on levan.

Results.

Pancreatic cancer cells cultured in ERS diet mimicking medium showed decreased levels of phospho-ERK1/2 and phospho-mTOR levels as compared to those cultured in standard medium. Consistently, xenograft pancreatic cancer mice subjected to ERS diet displayed a significant retard in tumor growth. In in vitro growth experiments the fecal microbial cultures from mice fed with ERS diet showed enhanced growth on residual substrates, higher production of formate and lactate and decreased amounts of propionate compared to fecal microbiota from mice fed with control diet.

Conclusion.

A positive effect of ERS diet on composition and metabolism of the mice fecal microbiota shown in vitro is associated with the decrease of tumor progression in the in vivo PC xenograft mouse model. These results demonstrate that engineered nutritional interventions could be supportive as synergistic approach to enhance the efficacy of existing cancer treatments in pancreatic cancer patients.

Examples of composition according to the present invention.

Composition 1

| | |
|---|---|
| casein | 140 gr; |
| L-cystine | 1 gr; |
| maltodestrine | 100 gr; |
| cellulose | 30 gr; |
| soybean oil | 15 gr; |
| lard | 5 gr; |
| Resistant Starch | 380 gr; |
| Mineral Mix | 2 gr; |
| dicalcium phosphate | 3.5 gr; |
| dicalcium carbonate | 1.5 gr; |
| potassium citrate | 4 gr; |
| Vitamins Mix | 2 gr; |
| Choline bitartrate | 0.5 gr. |

Composition 2

| | |
|---|---|
| casein | 260 gr; |
| L-cystine | 4 gr; |
| maltodestrine | 200 gr; |
| cellulose | 70 gr; |
| soybean oil | 35 gr; |
| lard | 30 gr; |
| Resistant Starch | 710 gr; |
| Mineral Mix | 15 gr; |
| dicalcium phosphate | 17 gr; |
| dicalcium carbonate | 8 gr; |
| potassium citrate | 20 gr; |
| Vitamins Mix | 15 gr; |
| Choline bitartrate | 4 gr. |

Composition 3

| | |
|---|---|
| casein | 200 gr; |
| L-cystine | 3 gr; |
| maltodestrine | 150 gr; |
| cellulose | 50 gr; |
| soybean oil | 25 gr; |
| lard | 20 gr; |
| Resistant Starch | 500 gr; |
| Mineral Mix | 10 gr; |
| dicalcium phosphate | 13 gr; |
| dicalcium carbonate | 5.5 gr; |
| potassium citrate | 16.5 gr; |
| Vitamins Mix | 10 gr; |
| Choline bitartrate | 2 gr. |

Composition 4

| | |
|---|---|
| casein | 190 gr; |
| L-cystine | 4 gr; |
| maltodestrine | 200 gr; |
| cellulose | 60 gr; |
| soybean oil | 35 gr; |
| lard | 15 gr; |
| Resistant Starch | 485 gr; |
| Mineral Mix | 14 gr; |
| dicalcium phosphate | 18 gr; |
| dicalcium carbonate | 5 gr; |
| potassium citrate | 14 gr; |
| Vitamins Mix | 12.5 gr; |
| Choline bitartrate | 2.5 gr. |

Composition 5

| | |
|---|---|
| casein | 215 gr; |
| L-cystine | 2.5 gr; |
| maltodestrine | 110 gr; |
| cellulose | 70 gr; |
| soybean oil | 30 gr; |
| lard | 22 gr; |
| Resistant Starch | 565 gr; |
| Mineral Mix | 8 gr; |
| dicalcium phosphate | 8 gr; |
| dicalcium carbonate | 7 gr; |
| potassium citrate | 10.5 gr; |
| Vitamins Mix | 7 gr; |
| Choline bitartrate | 2 gr. |

Composition 6

| | |
|---|---|
| casein | 175 gr; |
| L-cystine | 4 gr; |
| maltodestrine | 130 gr; |
| cellulose | 35 gr; |
| soybean oil | 25 gr; |
| lard | 25 gr; |
| Resistant Starch | 600 gr; |
| Mineral Mix | 10 gr; |
| dicalcium phosphate | 15 gr; |
| dicalcium carbonate | 6.5 gr; |
| potassium citrate | 20 gr; |
| Vitamins Mix | 8 gr; |
| Choline bitartrate | 1.5 gr. |

Composition 7

| | |
|---|---|
| casein | 260 gr; |
| L-cystine | 2 gr; |
| maltodestrine | 185 gr; |
| cellulose | 45 gr; |
| soybean oil | 20 gr; |
| lard | 15 gr; |
| Resistant Starch | 465 gr; |
| Mineral Mix | 12 gr; |
| dicalcium phosphate | 11 gr; |
| dicalcium carbonate | 6 gr; |
| potassium citrate | 18 gr; |
| Vitamins Mix | 13.5 gr; |
| Choline bitartrate | 2.5 gr. |

Composition 8

| | |
|---|---|
| casein | 230 gr; |
| L-cystine | 2 gr; |
| maltodestrine | 175 gr; |
| cellulose | 55 gr; |
| soybean oil | 20 gr; |
| lard | 14 gr; |
| Resistant Starch | 500 gr; |
| Mineral Mix | 8 gr; |
| dicalcium phosphate | 14 gr; |
| dicalcium carbonate | 7 gr; |
| potassium citrate | 16 gr; |
| Vitamins Mix | 12 gr; |
| Choline bitartrate | 2 gr. |

REFERENCES

1. Siegel R, Naishadham D and Jemal A. Cancer statistics, 2012. CA Cancer J Clin. 2012; 62(1):10-29.
2. D'Aronzo M, Vinciguerra M, Mazza T, Panebianco C, Saracino C, Pereira S P, Graziano P and Pazienza V. Fasting cycles potentiate the efficacy of gemcitabine treatment in in vitro and in vivo pancreatic cancer models. Oncotarget. 2015; 6(21):18545-18557.
3. Mathews E H and Liebenberg L. Short-term starvation for cancer control in humans. Exp Gerontol. 2013; 48(11): 1293.
4. Hursting S D, Lavigne J A, Berrigan D, Perkins S N and Barrett J C. Calorie restriction, aging, and cancer prevention: mechanisms of action and applicability to humans. Annu Rev Med. 2003; 54:131-152.
5. Raffaghello L, Lee C, Safdie F M, Wei M, Madia F, Bianchi G and Longo V D. Starvation-dependent differential stress resistance protects normal but not cancer cells against high-dose chemotherapy. Proc Natl Acad Sci USA. 2008; 105(24):8215-8220.
6. Pazienza V, la Torre A, Baorda F, Alfarano M, Chetta M, Muscarella L A, Battista C, Copetti M, Kotzot D, Kapelari K, Al-Abdulrazzaq D, Perlman K, Sochett E, Cole D E, Pellegrini F, Canaff L, et al. Identification and functional characterization of three NoLS (nucleolar localisation signals) mutations of the CDC73 gene. PLoS One. 2013; 8(12):e82292.
7. Benegiamo G, Vinciguerra M, Mazzoccoli G, Piepoli A, Andriulli A and Pazienza V. DNA methyltransferases 1 and 3b expression in Huh-7 cells expressing HCV core protein of different genotypes. Dig Dis Sci. 2012; 57(6): 1598-1603.
8. Rappa F, Greco A, Podrini C, Cappello F, Foti M, Bourgoin L, Peyrou M, Marino A, Scibetta N, Williams R, Mazzoccoli G, Federici M, Pazienza V and Vinciguerra M. Immunopositivity for histone macroH2A1 isoforms marks steatosis-associated hepatocellular carcinoma. PLoS One. 2013; 8(1):e54458.
9. Adamberg S, Tomson K, Vija H, Puurand M, Kabanova N, Visnapuu T, Jogi E, Alamae T and Adamberg K. Degradation of Fructans and Production of Propionic Acid by *Bacteroides thetaiotaomicron* are Enhanced by the Shortage of Amino Acids. Front Nutr. 2014; 1:21.
10. Kabanova N, Kazarjan A, Stulova I and Vilu R. Microcalorimetric study of growth of *Lactococcus lactis* IL1403 at different glucose concentrations in broth. Thermochimica Acta. 2009; (496):87-92.
11. Klindworth A, Pruesse E, Schweer T, Peplies J, Quast C, Horn M and Glockner F O. Evaluation of general 16S ribosomal RNA gene PCR primers for classical and next-generation sequencing-based diversity studies. Nucleic Acids Res. 2013; 41(1):e1.
12. Xia J, Sinelnikov I V, Han B and Wishart D S. MetaboAnalyst 3.0—making metabolomics more meaningful. Nucleic Acids Res. 2015; 43(W1):W251-257.
13. Apontes P, Leontieva O V, Demidenko Z N, Li F and Blagosklonny M V. Exploring long-term protection of normal human fibroblasts and epithelial cells from chemotherapy in cell culture. Oncotarget. 2011; 2(3):222-233.
14. Liu Y, Duysen E, Yaktine A L, Au A, Wang W and Birt D F. Nutritional energy restriction inhibits ERK but not JNK or p38 activity in the epidermis of SENCAR mice. Carcinogenesis. 2001; 22(4):607-612.
15. Longo V D and Fontana L. Intermittent supplementation with rapamycin as a nutritional restriction mimetic. Aging (Albany N.Y.). 2011; 3(11):1039-1040.
16. Nugent A P. (2005); "Health properties of resistant starch". Br Nutr Foundation Nutr Bull 30:27-5;
17. Sajilata, M. G.; Singhal, Rekha S.; Kulkarni, Pushpa R. (January 2006). "Resistant Starch—A Review". Comprehensive Reviews in Food Science and Food Safety. 5 (1): 1-17).

The invention claimed is:

1. A composition comprising:
casein in a weight ratio comprised between 12% and 26%;
L-cystine in a weight ratio comprised between 0.2 and 0.5%;
maltodextrin in a weight ratio comprised between 9% and 20%;
cellulose in a weight ratio comprised between 3% and 6.5%;
soybean oil in a weight ratio comprised between 1.5% and 3%;
lard in a weight ratio comprised between 1 and 3%;
resistant starch in a weight ratio comprised between 35 and 70%;
minerals in a weight ratio comprised between 0.5% and 1.5%;
dicalcium phosphate in a weight ratio comprised between 0.7 and 2%;
dicalcium carbonate in a weight ratio comprised between 0.1% and 1%;
potassium citrate in a weight ratio comprised between 0.9 and 2.2%;
vitamins in a weight ratio comprised between 0.5% and 1.5%;
choline bitartrate in a weight ratio comprised between 0.1 and 0.25%;
with respect to the total weight of the composition.

2. The composition according to claim 1, wherein the resistant starch is present in a weight ratio comprised between 45% and 55% with respect to the total weight of the composition.

3. Food product comprising the composition according to claim 1, characterized in that it is a liquid, a gel or a solid food product.

4. Kit comprising a first container (a) containing the composition according to claim 1 and a second container (b) containing water.

5. A method for treating a neoplastic disease comprising administering a composition according to claim 1.

6. The method according to claim 5, characterized in that it is administered orally or parenterally.

7. The method according to claim 5, characterized in that it is administered either combined with or in close temporal proximity to at least one further active principle.

8. The method according to claim 7, characterized in that said at least one further active principle is an antitumoral agent.

9. The method according to claim 8, wherein the antitumoral agent is a nucleoside analogue.

10. The method according to claim 5, wherein the neoplastic disease is selected from pancreatic cancer, non-small cell lung cancer, breast cancer and ovarian cancer.

11. The method according to claim 10, wherein the neoplastic disease is pancreatic cancer.

12. The method according to claim 5, wherein the composition comprises additional components selected from carbohydrates, minerals, salts and/or pharmaceutically acceptable derivatives and vitamins.

* * * * *